US010497478B2

(12) United States Patent
Jones et al.

(10) Patent No.: US 10,497,478 B2
(45) Date of Patent: Dec. 3, 2019

(54) REMOTE MONITORING AND DYNAMIC DOCUMENT MANAGEMENT SYSTEMS AND METHODS

(71) Applicant: FLORENCE HEALTHCARE, INC., Atlanta, GA (US)

(72) Inventors: Ryan Jones, Atlanta, GA (US); Andres Garcia, Atlanta, GA (US)

(73) Assignee: FLORENCE HEALTHCARE, INC., Atlanta, GA (US)

( * ) Notice: Subject to any disclaimer, the term of this patent is extended or adjusted under 35 U.S.C. 154(b) by 0 days.

(21) Appl. No.: 15/906,205

(22) Filed: Feb. 27, 2018

(65) Prior Publication Data

US 2018/0190389 A1  Jul. 5, 2018

Related U.S. Application Data

(63) Continuation of application No. 15/154,457, filed on May 13, 2016.

(60) Provisional application No. 62/161,552, filed on May 14, 2015.

(51) Int. Cl.
  *G16H 80/00* (2018.01)
  *G16H 10/20* (2018.01)
  *G06F 21/10* (2013.01)

(52) U.S. Cl.
  CPC ............ *G16H 80/00* (2018.01); *G06F 21/10* (2013.01); *G16H 10/20* (2018.01)

(58) Field of Classification Search
  CPC ......... G16H 80/00; G16H 10/20; G06F 21/10
  See application file for complete search history.

(56) References Cited

U.S. PATENT DOCUMENTS

| 9,378,205 B1* | 6/2016 | Schmidt | ............ G06F 17/30587 |
| 2013/0036127 A1* | 2/2013 | Simske | ............ G06F 17/30011 |
| | | | 707/754 |
| 2015/0071542 A1* | 3/2015 | Dahl | ................. G06K 9/00852 |
| | | | 382/177 |

* cited by examiner

*Primary Examiner* — Linh Giang Le
(74) *Attorney, Agent, or Firm* — Eversheds Sutherland (US) LLP

(57) ABSTRACT

Systems, methods, and computer-readable media are disclosed for remote monitoring and dynamic document management. Example methods may include receiving a first document from a device driver associated with a hardware device, identifying a clinical trial identifier associated with the first document based at least in part on metadata associated with the first document, and determining a first document type of the first document by analyzing contents of the first document. Methods may include managing user permission to access the first document. Methods may further include identifying a folder associated with the clinical trial identifier at which to store the first document based at least in part on the first document type, and assigning a first document state to the first document based at least in part on the first document type of the first document.

20 Claims, 10 Drawing Sheets

REMOTE MONITORING AND DYNAMIC DOCUMENT MANAGEMENT SYSTEMS AND METHODS

CROSS-REFERENCE TO RELATED APPLICATIONS

This application is a continuation of U.S. application Ser. No. 15/154,457, filed May 13, 2016, which claims priority to U.S. Provisional Application Ser. No. 62/161,552, filed May 14, 2015, entitled "Remote Monitoring and Dynamic Document Management Systems and Methods", the entire contents of which are incorporated by reference herein.

BACKGROUND

Clinical trials or research studies may be performed to determine an effectiveness or safety of medical treatments, such as medical procedures, drugs, or other treatments, for humans. Clinical trials may include clinical trial sites that conduct clinical trials or research studies on various patients and collect data that may be used to determine changes in patient health. Data collected by clinical trials may be communicated to other parties, such as a sponsor of a clinical trial, and may be subject to auditing or monitoring for accuracy and/or verification. Documents created for clinical trials may be subject to certain requirements and may need to be categorized so as to regulate access and tasks by different users.

BRIEF DESCRIPTION OF THE DRAWINGS

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. In the drawings, the left-most digit(s) of a reference numeral may identify the drawing in which the reference numeral first appears. The use of the same reference numerals indicates similar, but not necessarily the same or identical components. However, different reference numerals may be used to identify similar components as well. Various embodiments may utilize elements or components other than those illustrated in the drawings, and some elements and/or components may not be present in various embodiments. The use of singular terminology to describe a component or element may, depending on the context, encompass a plural number of such components or elements and vice versa. For example, the term "a clinical trial identifier" can refer to one or more identifiers and clinical trials.

DETAILED DESCRIPTION

Overview

This disclosure relates to, among other things, systems, methods, computer-readable media, techniques, and methodologies for remote monitoring and dynamic document management. Clinical trials or research studies may be performed to determine or evaluate safety and/or effectiveness of medical treatments on humans. Medical treatments may include medical procedures, medicines, drugs, medical strategies, and other medical treatments. Clinical trials or research studies may be organized and conducted by several parties. For example, a clinical trial may include one or more sponsors that may support or finance the clinical trial, one or more clinical trial sites that conduct clinical trials, one or more investigators that manage clinical trials and may execute documents, and one or more monitors that may audit data collected during a clinical trial. Sponsors may be government organizations, private companies, universities, or other organizations. Monitors may be employed by sponsors or contract research organizations that implement a clinical trial on behalf of a sponsor. Clinical trial sites or research sites may be sites at which the clinical trial is conducted or performed. Clinical trial sites may perform or otherwise facilitate implementation of clinical trials and may collect data points for patients or subjects of clinical trials. The data points collected by clinical trial sites may be evaluated to determine effectiveness and/or safety of the medical treatment being tested. Data generated by clinical trial sites, which may be referred to as end points, may be subject to validation, verification, or auditing. For example, government organizations may regulate auditing or verification of clinical trial data. Accordingly, clinical trials may also include monitors or other parties that validate clinical trial data. Monitors, which may be principal investigators, may monitor or review data generated by a clinical trial site for accuracy, completeness, and other metrics, and may authenticate results or findings of a clinical trial.

In order to monitor clinical trial site data, documents with patient information and/or data points collected by a clinical trial site may be communicated to monitors or other parties. The systems, methods, computer-readable media, techniques, and methodologies for remote monitoring and dynamic document management described herein may facilitate efficient document and information transfer between parties to a clinical trial and may further facilitate tracking of requests for clinical trial information, while protecting personally identifiable information and other sensitive patient information, or prescribing specific actions by parties. Embodiments of the disclosure may further facilitate compliance with governmental regulations, including, for example, regulations related to document archiving, patient information and privacy protection, wet and dry document signature regulations, and other government regulations.

Figure 1:
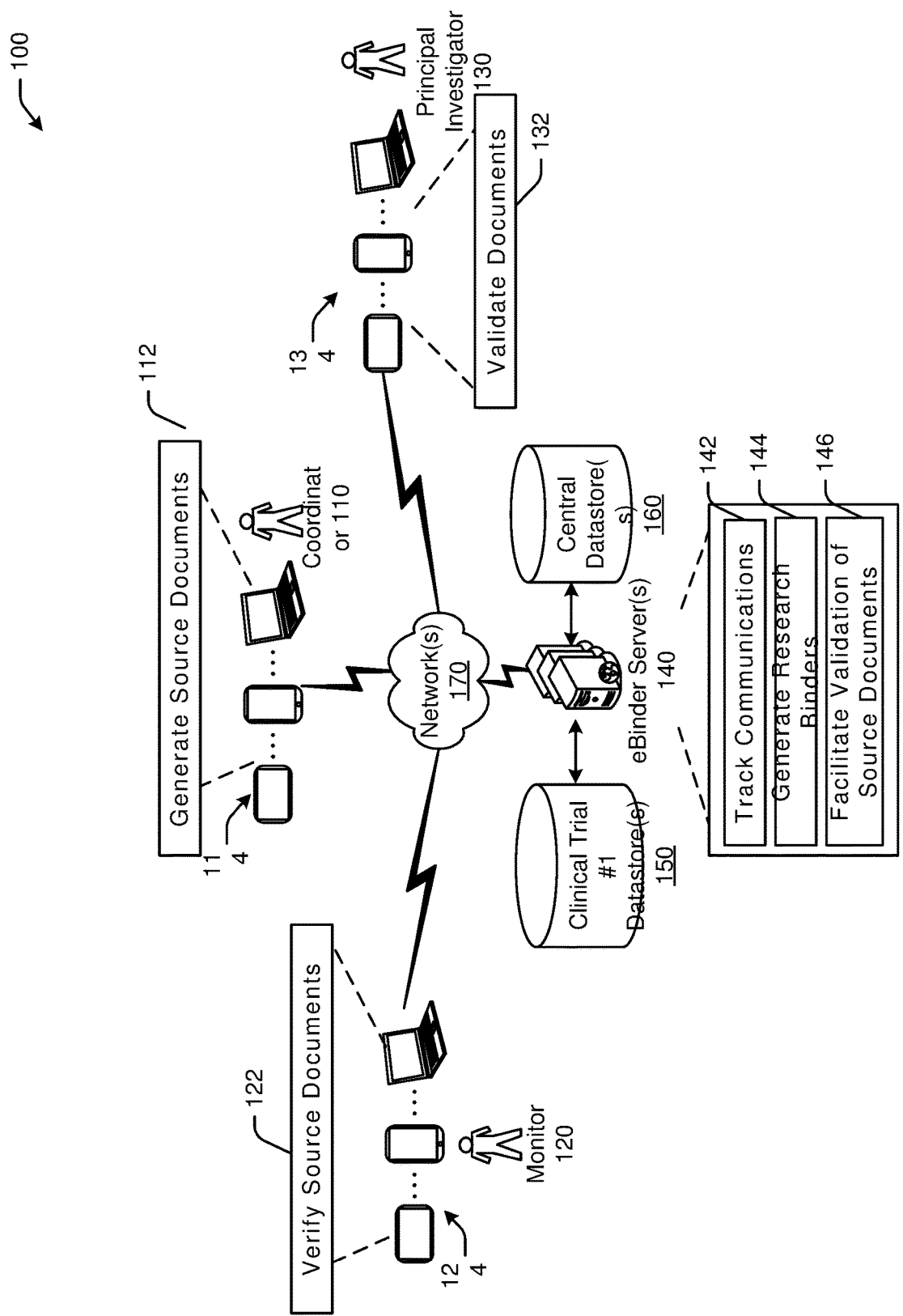
FIG. 1 is a schematic diagram of an example remote monitoring and dynamic document management system in accordance with one or more example embodiments of the disclosure.

Referring to FIG. 1, an example environment 100 of a remote monitoring and dynamic document management system with example functionality is illustrated with a coordinator 110, a monitor 120, a principal investigator 130, and one or more eBinder server(s) 140. The coordinator 110 may be located at a clinical trial site or a research site and may facilitate or conduct a clinical trial. The coordinator 110 may collect data from patients that are subjects of the clinical trial and may create, handle, or store documents for clinical trials. The coordinator 110 may generate relevant documents 112 (e.g., source and regulatory documents) by inputting data at a coordinator device 114. The monitor 120 may be a sponsor of a clinical trial or affiliated with a sponsor and may verify documents 122 that are generated by clinical trial site. For example, the monitor 120 may receive relevant documents at a monitor device 124 from the coordinator device 114 via one or more network(s) 170. The monitor 120 may be a contract research organization (CRO) and may verify the end points provided by the coordinator 110. The principal investigator 130 may validate documents 132. For example, the principal investigator 130 may receive relevant documents at a principal investigator device 134 via the network 170 from the coordinator 110 via the coordinator device 114 and/or the monitor 120 via the monitor device 124. The principal investigator 130 may sign off documents associated with a clinical trial, such as source documents with end points or results of the clinical trial. Example types of documents or source documents may include, without limitation, electronic health records, end points in Case Report Forms, patient data, or the like.

The coordinator device 114, the monitor device 124, and the principal investigator device 134 may be in communication with the eBinder server 140 via the network 170. The eBinder server 140 may be configured to track communications 142 between any of the coordinator 110, the monitor 120, or the principal investigator 130. The eBinder server 140 may further be configured to generate research binders 144 for clinical trials. Research binders may be virtual folders generated by the eBinder server 140 that may include some or all relevant documentation, messages, evidence, data, and other information for particular clinical trials. Research binders generated by the eBinder server 140 may be accessed by appropriate parties, as described herein, and may provide statuses of various tasks or queries/requests associated with a clinical trial. The eBinder server 140 may further be configured to facilitate validation of source documents 146 that are generated by the coordinator 110, for example, by tracking a status of a task or query/request made by the principal investigator 130, among other functions. The eBinder server 140 may be in communication with one or more datastores. For example, as shown in FIG. 1, the eBinder server 140 may be in communication with a Clinical Trial #1 datastore 150 that may be configured to receive and/or store data associated with a particular clinical trial. Metrics associated with a particular clinical trial, such as timeliness of task response, accuracy, responsiveness, and other metrics may be tracked in a dashboard presented by the eBinder server 140. Metrics may be generated by the eBinder server 140 and may be used to evaluate clinical trial or research site overall quality. The eBinder server 140 may be in communication with a central datastore 160 that may serve as a backup for data generated by or information collected by the eBinder server 140. In one example, research binders generated by the eBinder server 140 may be stored at the central datastore 160 and may be accessible by one or more authorized parties. While example embodiments of the disclosure may be described in the context of source documents, it should be appreciated that the disclosure is more broadly applicable to any form of medical documentation and/or medical records consumable on any suitable user device including, without limitation, a smartphone, a tablet, a wearable device, or any other suitable device.

Example embodiments of the disclosure provide a number of technical features or technical effects. For example, in accordance with example embodiments of the disclosure, validation of documents may be facilitated by managing source documents, generating task requests and tracking task statuses, redacting sensitive information via spatial propagation, generating virtual binders with automatically captured messages and message attachments, prescribing tasks, among other technical features. The above examples of technical features and/or technical effects of example embodiments of the disclosure are merely illustrative and not exhaustive.

One or more illustrative embodiments of the disclosure have been described above. The above-described embodiments are merely illustrative of the scope of this disclosure and are not intended to be limiting in any way. Accordingly, variations, modifications, and equivalents of embodiments disclosed herein are also within the scope of this disclosure. The above-described embodiments and additional and/or alternative embodiments of the disclosure will be described in detail hereinafter through reference to the accompanying drawings.

Illustrative Device Architecture

Figure 2:
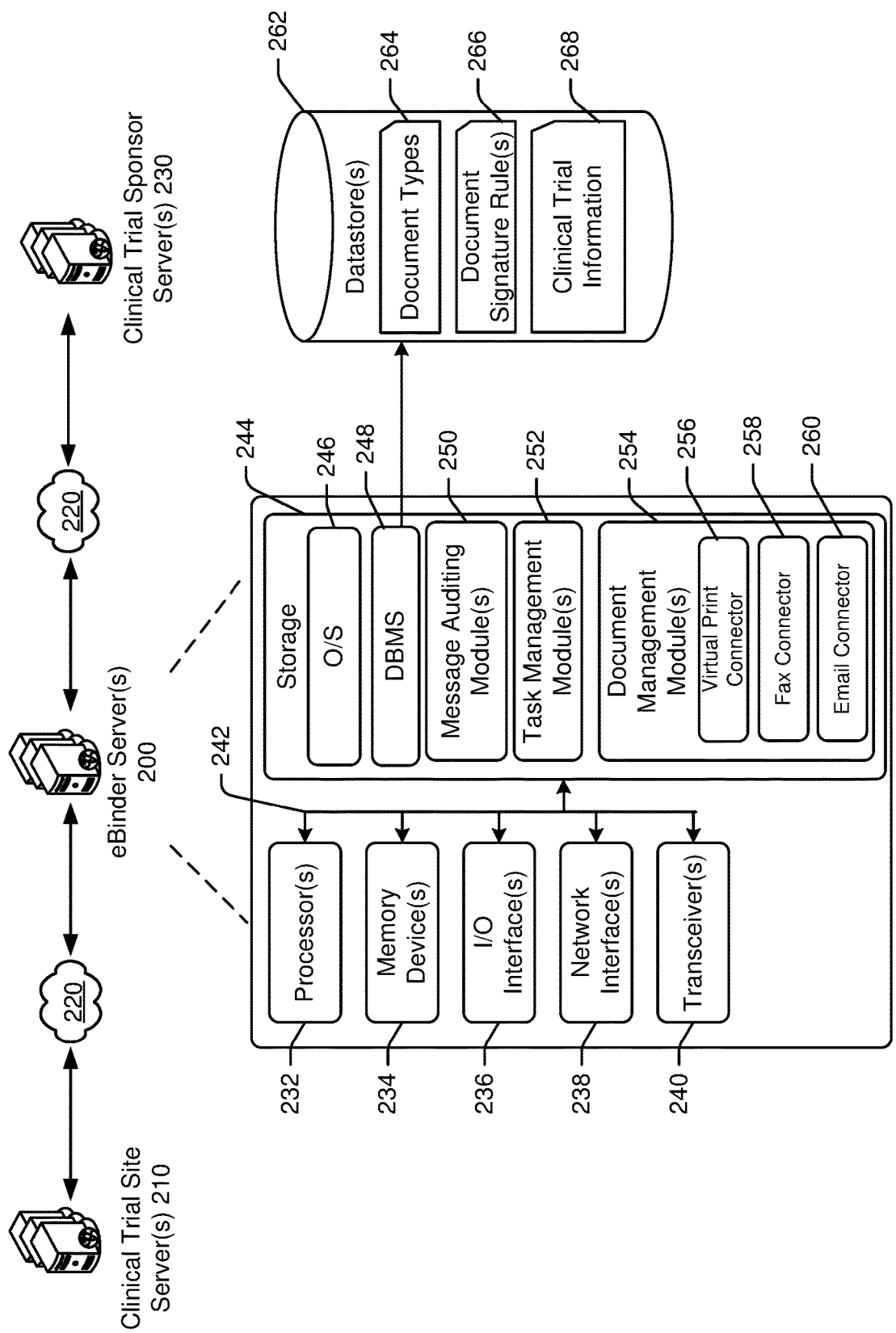
FIG. 2 is a schematic illustration of example computer architecture of an eBinder server user device in accordance with one or more example embodiments of the disclosure.

FIG. 2 is a schematic block diagram of one or more illustrative eBinder server(s) 200 in communication with one or more clinical trial site server(s) 210 and one or more clinical trial sponsor server(s) 230 via one or more network(s) 220 in accordance with one or more example embodiments of the disclosure. The eBinder server 200 may correspond to the eBinder server 140 of FIG. 1, or may be a different server. Similarly, the network(s) 220 may correspond to the network 170 of FIG. 1.

The eBinder server 200 may be configured to communicate via network(s) 220 with one or more servers, user devices, or the like. The network(s) 220 may include, but are not limited to, any one or more different types of communications networks such as, for example, cable networks, public networks (e.g., the Internet), private networks (e.g., frame-relay networks), wireless networks, cellular networks, telephone networks (e.g., a public switched telephone network), or any other suitable private or public packet-switched or circuit-switched networks. Further, the network(s) 220 may have any suitable communication range associated therewith and may include, for example, global networks (e.g., the Internet), metropolitan area networks (MANs), wide area networks (WANs), local area networks (LANs), or personal area networks (PANs). In addition, the network(s) 220 may include communication links and associated networking devices (e.g., link-layer switches, routers, etc.) for transmitting network traffic over any suitable type of medium including, but not limited to, coaxial cable, twisted-pair wire (e.g., twisted-pair copper wire), optical fiber, a hybrid fiber-coaxial (HFC) medium, a microwave medium, a radio frequency communication medium, a satellite communication medium, or any combination thereof.

In an illustrative configuration, the eBinder server 200 may include one or more processors (processor(s)) 232, one or more memory devices 234 (generically referred to herein as memory 234), one or more input/output ("I/O") interface(s) 236, one or more network interfaces 238, one or more transceivers 240, and data storage 244. The eBinder server 200 may further include one or more buses 242 that functionally couple various components of the eBinder server 200. The eBinder server 200 may further include one or more antennas that may include, without limitation, a cellular antenna for transmitting or receiving signals to/from a cellular network infrastructure, an antenna for transmitting or receiving Wi-Fi signals to/from an access point (AP), a Global Navigation Satellite System (GNSS) antenna for receiving GNSS signals from a GNSS satellite, a Bluetooth antenna for transmitting or receiving Bluetooth signals, a Near Field Communication (NFC) antenna for transmitting or receiving NFC signals, and so forth. These various components will be described in more detail hereinafter.

The bus(es) 242 may include at least one of a system bus, a memory bus, an address bus, or a message bus, and may permit exchange of information (e.g., data (including computer-executable code), signaling, etc.) between various components of the eBinder server 200. The bus(es) 242 may include, without limitation, a memory bus or a memory controller, a peripheral bus, an accelerated graphics port, and so forth. The bus(es) 242 may be associated with any suitable bus architecture including, without limitation, an Industry Standard Architecture (ISA), a Micro Channel Architecture (MCA), an Enhanced ISA (EISA), a Video Electronics Standards Association (VESA) architecture, an Accelerated Graphics Port (AGP) architecture, a Peripheral Component Interconnects (PCI) architecture, a PCI-Express architecture, a Personal Computer Memory Card International Association (PCMCIA) architecture, a Universal Serial Bus (USB) architecture, and so forth.

The memory 234 of the eBinder server 200 may include volatile memory (memory that maintains its state when supplied with power) such as random access memory (RAM) and/or non-volatile memory (memory that maintains its state even when not supplied with power) such as read-only memory (ROM), flash memory, ferroelectric RAM (FRAM), and so forth. In certain example embodiments, volatile memory may enable faster read/write access than non-volatile memory. However, in certain other example embodiments, certain types of non-volatile memory (e.g., FRAM) may enable faster read/write access than certain types of volatile memory.

In various implementations, the memory 234 may include multiple different types of memory such as various types of static random access memory (SRAM), various types of dynamic random access memory (DRAM), various types of unalterable ROM, and/or writeable variants of ROM such as electrically erasable programmable read-only memory (EEPROM), flash memory, and so forth. The memory 234 may include main memory as well as various forms of cache memory such as instruction cache(s), data cache(s), translation lookaside buffer(s) (TLBs), and so forth. Further, cache memory such as a data cache may be a multi-level cache organized as a hierarchy of one or more cache levels (L1, L2, etc.).

The data storage 244 may include removable storage and/or non-removable storage including, but not limited to, magnetic storage, optical disk storage, and/or tape storage. The data storage 244 may provide non-volatile storage of computer-executable instructions and other data. The memory 234 and the data storage 244, removable and/or non-removable, are examples of computer-readable storage media (CRSM) as that term is used herein.

The data storage 244 may store computer-executable code, instructions, or the like that may be loadable into the memory 234 and executable by the processor(s) 232 to cause the processor(s) 232 to perform or initiate various operations. The data storage 244 may additionally store data that may be copied to memory 234 for use by the processor(s) 232 during the execution of the computer-executable instructions. Moreover, output data generated as a result of execution of the computer-executable instructions by the processor(s) 232 may be stored initially in memory 234, and may ultimately be copied to data storage 244 for non-volatile storage.

More specifically, the data storage 244 may store one or more operating systems (O/S) 246, one or more database management systems (DBMS) 248, and one or more program modules, applications, or the like such as, for example, one or more message auditing module(s) 250, one or more task management module(s) 252, and one or more document management module(s) 254. Any of the program modules may include one or more sub-modules. For example, the document management module 254 may include a virtual print connector sub-module 256, a fax connector sub-module 258, and an email connector sub-module 260. Any of the modules depicted in FIG. 2 may include computer-executable code, instructions, or the like that may be loaded into the memory 234 for execution by one or more of the processor(s) 232. Further, any data stored in the data storage 244 may be loaded into the memory 234 for use by the processor(s) 232 in executing computer-executable code. In addition, any data potentially stored in one or more datastores 262 may be accessed via the DBMS 248 and loaded in the memory 234 for use by the processor(s) 232 in executing computer-executable code. In the illustrated example, the datastores 262 may include document types 264 representative of types or categories of documents processed or received by the eBinder server 200. The datastores 262 may include document signature rule(s) 266, which may include rules related to documents that require signatures, types of signatures required (e.g., wet or dry signatures, etc.), and other rules. The datastores 262 may include clinical trial information 268 which may include clinical trial identifiers, patient identifiers, user authorization information, and other clinical trial information.

The processor(s) 232 may be configured to access the memory 234 and execute computer-executable instructions loaded therein. For example, the processor(s) 232 may be configured to execute computer-executable instructions of the various program modules of the user eBinder server 200 to cause or facilitate various operations to be performed in accordance with one or more embodiments of the disclosure. The processor(s) 232 may include any suitable processing unit capable of accepting data as input, processing the input data in accordance with stored computer-executable instructions, and generating output data. The processor(s) 232 may include any type of suitable processing unit including, but not limited to, a central processing unit, a microprocessor, a Reduced Instruction Set Computer (RISC) microprocessor, a Complex Instruction Set Computer (CISC) microprocessor, a microcontroller, an Application Specific Integrated Circuit (ASIC), a Field-Programmable Gate Array (FPGA), a System-on-a-Chip (SoC), a digital signal processor (DSP), and so forth. Further, the processor(s) 232 may have any suitable microarchitecture design that includes any number of constituent components such as, for example, registers, multiplexers, arithmetic logic units, cache controllers for controlling read/write operations to cache memory, branch predictors, or the like. The microarchitecture design of the processor(s) 232 may be capable of supporting any of a variety of instruction sets.

Referring now to functionality supported by the various program modules depicted in FIG. 2, the message auditing module(s) 250 may include computer-executable instructions, code, or the like that responsive to execution by one or more of the processor(s) 232 may perform functions including, but not limited to, track some or all email communications between parties to a clinical trial, such as coordinators, investigators, and/or sponsors. Computer-executable instructions of the message auditing module(s) 250 may be executed to store, categorize, organize, or facilitate searching of email or other text messages of a clinical trial.

The task management module(s) 252 may include computer-executable instructions, code, or the like that responsive to execution by one or more of the processor(s) 232 may perform functions including, but not limited to, generating queries, identifying clinical trials associated with queries and task queues, and tracking task responses. The task management module(s) 252 may further include computer-executable instructions, code, or the like that responsive to execution by one or more of the processor(s) 232 to facilitate access to documents uploaded in response to queries by permitted users.

The document management module(s) 254 may include computer-executable instructions, code, or the like that responsive to execution by one or more of the processor(s) 232 may perform functions including, but not limited to, organize, store, capture, and present documents. Computer-executable instructions of the document management module(s) 254 may be executed to redact portions of documents, as described herein.

Referring now to other illustrative components depicted as being stored in the data storage 244, the O/S 246 may be loaded from the data storage 244 into the memory 234 and may provide an interface between other application software executing on the eBinder server 200 and hardware resources of the eBinder server 200. More specifically, the O/S 246 may include a set of computer-executable instructions for managing hardware resources of the eBinder server 200 and for providing common services to other application programs (e.g., managing memory allocation among various application programs). In certain example embodiments, the O/S 246 may control execution of the other program modules to dynamically enhance characters for content rendering. The O/S 246 may include any operating system now known or which may be developed in the future including, but not limited to, any server operating system, any mainframe operating system, or any other proprietary or non-proprietary operating system.

The DBMS 248 may be loaded into the memory 234 and may support functionality for accessing, retrieving, storing, and/or manipulating data stored in the memory 234 and/or data stored in the data storage 244. The DBMS 248 may use any of a variety of database models (e.g., relational model, object model, etc.) and may support any of a variety of task languages. The DBMS 248 may access data represented in one or more data schemas and stored in any suitable data repository including, but not limited to, databases (e.g., relational, object-oriented, etc.), file systems, flat files, distributed datastores in which data is stored on more than one node of a computer network, peer-to-peer network datastores, or the like. In those example embodiments in which the eBinder server 200 is a mobile device, the DBMS 248 may be any suitable light-weight DBMS optimized for performance on a mobile device.

Referring now to other illustrative components of the eBinder server 200, one or more input/output (I/O) interfaces 236 may be provided that may facilitate the receipt of input information by the eBinder server 200 from one or more I/O devices as well as the output of information from the eBinder server 200 to the one or more I/O devices. The I/O devices may include, for example, one or more user interface devices that facilitate interaction between a user and the eBinder server 200 including, but not limited to, a display, a keypad, a pointing device, a control panel, a touch screen display, a gesture capture or detection device, a remote control device, a microphone, a speaker, and so forth. The I/O devices may further include, for example, any number of peripheral devices such as data storage devices, printing devices, and so forth.

The eBinder server 200 may further include one or more network interfaces 238 via which the eBinder server 200 may communicate with any of a variety of other systems, platforms, networks, devices, and so forth. Such communication may occur via any of the types of networks previously described.

The eBinder server 200 may include one or more antenna(s). The one or more antenna(s) may include any suitable type of antenna depending, for example, on the communications protocols used to transmit or receive signals via the antenna(s). Non-limiting examples of suitable antennas may include directional antennas, non-directional antennas, dipole antennas, folded dipole antennas, patch antennas, multiple-input multiple-output (MIMO) antennas, or the like. The antenna(s) may be communicatively coupled to one or more transceivers 240 or radio components to which or from which signals may be transmitted or received.

As previously described, the antenna(s) may include a cellular antenna configured to transmit or receive signals in accordance with established standards and protocols, such as Global System for Mobile Communications (GSM), 3G standards (e.g., Universal Mobile Telecommunications System (UMTS), Wideband Code Division Multiple Access (W-CDMA), CDMA2000, etc.), 4G standards (e.g., Long-Term Evolution (LTE), WiMax, etc.), direct satellite communications, or the like.

The antenna(s) may additionally, or alternatively, include a Wi-Fi antenna configured to transmit or receive signals in accordance with established standards and protocols, such as the IEEE 802.11 family of standards, including via 2.4 GHz channels (e.g. 802.11b, 802.11g, 802.11n), 5 GHz channels (e.g. 802.11n, 802.11ac), or 60 GHZ channels (e.g. 802.11ad). In alternative example embodiments, the antenna(s) may be configured to transmit or receive radio frequency signals within any suitable frequency range forming part of the unlicensed portion of the radio spectrum.

The antenna(s) may additionally, or alternatively, include a GNSS antenna configured to receive GNSS signals from three or more GNSS satellites carrying time-position information to triangulate a position therefrom. Such a GNSS antenna may be configured to receive GNSS signals from any current or planned GNSS such as, for example, the Global Positioning System (GPS), the GLONASS System, the Compass Navigation System, the Galileo System, or the Indian Regional Navigational System.

The transceiver(s) 240 may include any suitable radio component(s) for—in cooperation with the antenna(s)—transmitting or receiving radio frequency (RF) signals in the bandwidth and/or channels corresponding to the communications protocols utilized by the eBinder server 200 to communicate with other devices. The transceiver(s) 240 may include hardware, software, and/or firmware for modulating, transmitting, or receiving—potentially in cooperation with any of antenna(s)—communications signals according to any of the communications protocols discussed above including, but not limited to, one or more Wi-Fi and/or Wi-Fi direct protocols, as standardized by the IEEE 802.11 standards, one or more non-Wi-Fi protocols, or one or more cellular communications protocols or standards. The transceiver(s) 240 may further include hardware, firmware, or software for receiving GNSS signals. The transceiver(s) 240 may include any known receiver and baseband suitable for communicating via the communications protocols utilized by the eBinder server 200. The transceiver(s) 240 may further include a low noise amplifier (LNA), additional signal amplifiers, an analog-to-digital (A/D) converter, one or more buffers, a digital baseband, or the like.

It should be appreciated that the program modules, applications, computer-executable instructions, code, or the like depicted in FIG. 2 as being stored in the data storage 244 are merely illustrative and not exhaustive and that processing described as being supported by any particular module may alternatively be distributed across multiple modules or performed by a different module. In addition, various program module(s), script(s), plug-in(s), Application Programming Interface(s) (API(s)), or any other suitable computer-executable code hosted locally on the eBinder server 200, and/or hosted on other computing device(s) accessible via one or more networks, may be provided to support functionality provided by the program modules, applications, or computer-executable code depicted in FIG. 2 and/or additional or alternate functionality. Further, functionality may be modularized differently such that processing described as being supported collectively by the collection of program modules depicted in FIG. 2 may be performed by a fewer or greater number of modules, or functionality described as being supported by any particular module may be supported, at least in part, by another module. In addition, program modules that support the functionality described herein may form part of one or more applications executable across any number of systems or devices in accordance with any suitable computing model such as, for example, a client-server model, a peer-to-peer model, and so forth. In addition, any of the functionality described as being supported by any of the program modules depicted in FIG. 2 may be implemented, at least partially, in hardware and/or firmware across any number of devices.

It should further be appreciated that the eBinder server 200 may include alternate and/or additional hardware, software, or firmware components beyond those described or depicted without departing from the scope of the disclosure. More particularly, it should be appreciated that software, firmware, or hardware components depicted as forming part of the eBinder server 200 are merely illustrative and that some components may not be present or additional components may be provided in various embodiments. While various illustrative program modules have been depicted and described as software modules stored in data storage 244, it should be appreciated that functionality described as being supported by the program modules may be enabled by any combination of hardware, software, and/or firmware. It should further be appreciated that each of the above-mentioned modules may, in various embodiments, represent a logical partitioning of supported functionality. This logical partitioning is depicted for ease of explanation of the functionality and may not be representative of the structure of software, hardware, and/or firmware for implementing the functionality. Accordingly, it should be appreciated that functionality described as being provided by a particular module may, in various embodiments, be provided at least in part by one or more other modules. Further, one or more depicted modules may not be present in certain embodiments, while in other embodiments, additional modules not depicted may be present and may support at least a portion of the described functionality and/or additional functionality. Moreover, while certain modules may be depicted and described as sub-modules of another module, in certain embodiments, such modules may be provided as independent modules or as sub-modules of other modules.

While described in detail with respect to the eBinder server 200, the clinical trial site server 210 and/or the clinical trial sponsor server 230 may include some or all of the components or modules described with respect to the eBinder server 200.

Program modules, applications, or the like disclosed herein may include one or more software components including, for example, software objects, methods, data structures, or the like. Each such software component may include computer-executable instructions that, responsive to execution, cause at least a portion of the functionality described herein (e.g., one or more operations of the illustrative methods described herein) to be performed.

A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform.

Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database task or search language, or a report writing language. In one or more example embodiments, a software component comprising instructions in one of the foregoing examples of programming languages may be executed directly by an operating system or other software component without having to be first transformed into another form.

A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Software components may invoke or be invoked by other software components through any of a wide variety of mechanisms. Invoked or invoking software components may comprise other custom-developed application software, operating system functionality (e.g., device drivers, data storage (e.g., file management) routines, other common routines and services, etc.), or third-party software components (e.g., middleware, encryption, or other security software, database management software, file transfer or other network communication software, mathematical or statistical software, image processing software, and format translation software).

Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages, but may invoke software components written in another programming language.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or operations specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or operations specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program modules, or other data transmitted within a data signal, such as a carrier wave, or other transmission. However, as used herein, CRSM does not include CRCM.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Illustrative Processes and Use Cases

Figure 3:
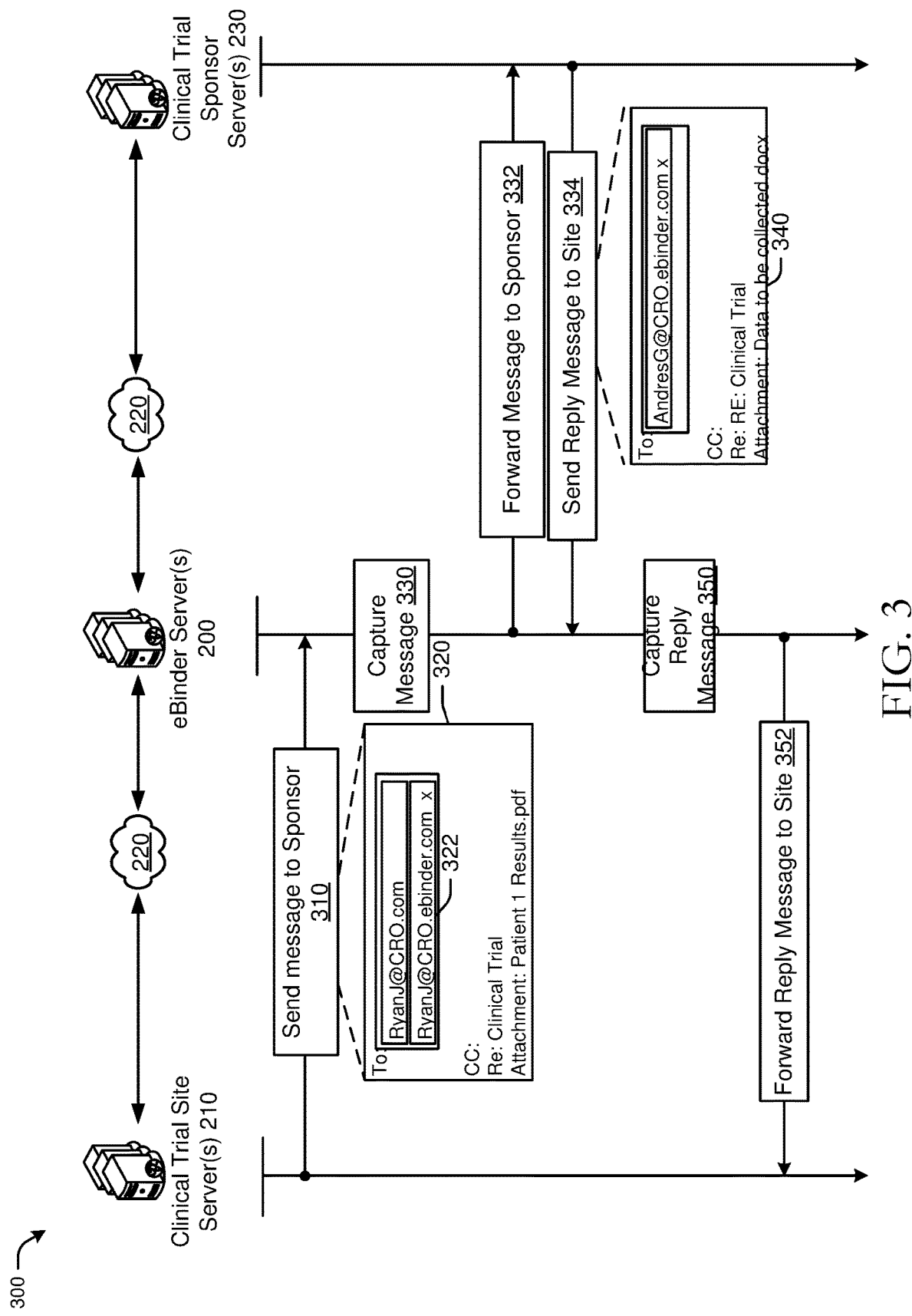
FIG. 3 is an example data flow diagram over time of an illustrative method for remote monitoring and dynamic document management in accordance with one or more example embodiments of the disclosure.

FIG. 3 is an example data flow 300 of a message auditing use case in accordance with one or more embodiments of the disclosure. Coordinators, monitors, and investigators may communicate via email or other messaging protocols. For example, documents related to a clinical trial may be emailed as email attachments from a coordinator to a monitor while exchanging details during remote monitoring activities. Embodiments of the disclosure may be configured to automatically identify, collect, and/or capture/store emails and email attachments related to a clinical trial that are communicated from one party to another. In FIG. 3, the data flow 300 illustrates communications over time between the eBinder server 200, the clinical trial site server 210, and the clinical trial sponsor server 230 illustrated in FIG. 2. One or more operations or communications illustrated in FIG. 3 may occur concurrently or partially concurrently, while illustrated as discrete communications or operations for ease of illustration.

At communication 310, a coordinator may send a message 320 to a sponsor via a user account associated with the coordinator. The message may include text and an email attachment or attached file, as shown in FIG. 3, that includes patient data or patient results. The coordinator may send the message 320 via the clinical trial site server 210, and may address the message 320 to the sponsor at a designated email address 322. The designated email address 322 may be a custom email address generated for the sponsor for a particular clinical trial or for use with multiple clinical trials associated with the coordinator or sponsor. In some embodiments, the custom email address may be associated with a contacts manager that applies information such as first and last name associated with a default user email address to the custom email address, such that the custom email address is associated with the default email address for a user. Such embodiments may facilitate downloading or syncing of contacts in email systems. Users may be able to select either the default email address or the custom email address when sending emails to a user. By sending the message 320 to the designated email address, the coordinator may intend for the email or message 320 and/or the email attachment to be captured and associated with a particular clinical trial, or to kick off a prescribed set of tasks in the system.

The eBinder server 200 may receive the message 320 from the clinical trial site server 210. The eBinder server 200 may identify a clinical trial identifier associated with the message 320. In some embodiments, the eBinder server 200 may identify the clinical trial identifier based at least in part on the coordinator user account form which the message 320 was sent or a user account associated with an intended recipient of the message 320, text or other contents included in the message 320, such as a subject line, contents included in the attached file, such as a filename, via a stack overflow process, or another method. Upon identifying a clinical trial identifier that the message 320 is associated with, the eBinder server 200 may store a copy of the message 320 in a folder associated with the clinical trial identifier. Specifically, at operation 330, the eBinder server 200 may capture the message 330 and store the contents of the message 330, along with, in some embodiments, the email attachment. For example, the eBinder server 200 may store contents of the message 320 at a central datastore in a folder designated for communications or messages associated with a particular clinical trial. The eBinder server 200 may further store meta attributes of the message 320, such as timestamps. In one example, computer-executable instructions of the message auditing module(s) 250 may be executed to identify a clinical trial associated with the message 320, and to capture or store the message contents and email attachment.

The eBinder server 200 may identify a sponsor user account indicative of the intended recipient of the message 320, and may identify an email address associated with the sponsor user account. The eBinder server 200 may forward the message 320 to the sponsor email address at communication 332 after capturing the message contents and, in some embodiments, the message attachments.

The clinical trial sponsor server 230 may receive the forwarded message from the eBinder server 200. At communication 334, the sponsor may reply to the message 320 from the coordinator via the sponsor email account by sending a reply message 340. The reply message 340 may include an attachment, such as a request for patient information. The eBinder server 200 may receive the reply message 340 and, at operation 350, the eBinder server 200 may capture the reply message 340 and the attachment. In the illustrated example, the eBinder server 200 may receive the reply message 340 from the sponsor email address, and may determine that the reply message 340 is a reply to the message 320, for example via analysis of the subject line of the email. The eBinder server 200 may store the reply message 340 in the folder that was previously identified for the original message 320, and may forward the reply message 340 to the coordinator email or user account at operation 352. Accordingly, the eBinder server 200 may automatically store and organize messages associated with a clinical trial for reference by authorized parties.

Figure 4:
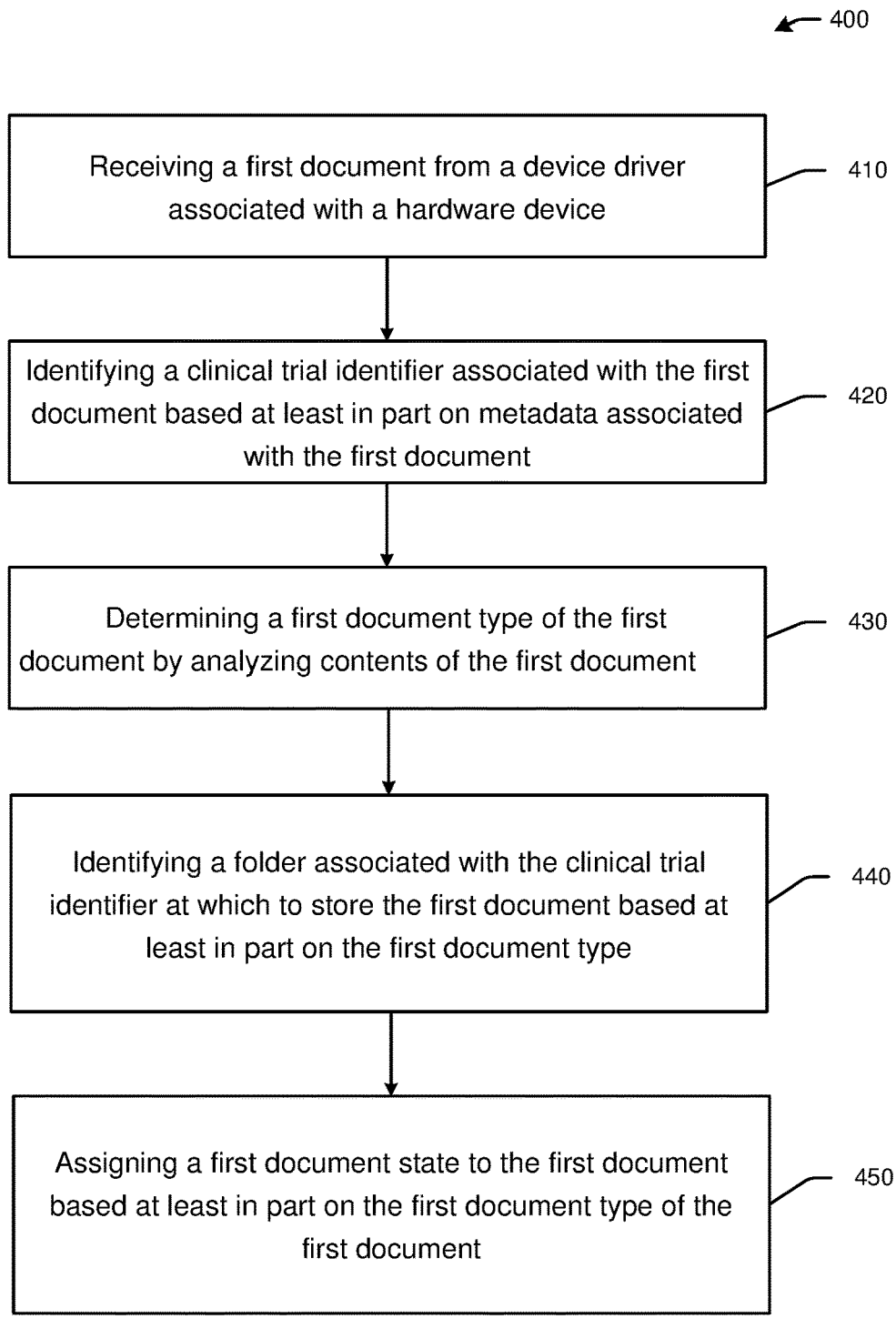
FIG. 4 is an example process flow diagram of an illustrative method for remote monitoring and dynamic document management in accordance with one or more example embodiments of the disclosure.

FIG. 4 is a process flow diagram of an illustrative method 400 for remote monitoring and dynamic document management in accordance with one or more example embodiments of the disclosure. In FIG. 4, computer-executable instructions of one or more module(s) of a eBinder server, such as the document management module(s) 254 of the eBinder server 200 of FIGS. 2-3, may be executed to manage documents associated with a clinical trial. Embodiments of the disclosure may be configured to collect, sign, and/or share source documents as evidence of, or to otherwise substantiate, work performed at a clinical trial site. Documents may have several different document types and sources, such as electronic health records, lab reports, images from imaging systems, third-party documents from doctor offices, and other document types and sources. Embodiments of the disclosure may automatically collect documents from any number of sources and of different document types and may store and categorize the collected or captured documents in respective clinical trial folders and/or virtual research binders. As described herein, embodiments of the disclosure may collect, obtain, or capture documents in a number of methods, including software connectors such as virtual printers, e-fax ports, email parsers, uploaded documents, and others. Connectors may be configured to import documents from different sources and may be installed at local user devices. Connectors, such as a virtual printer connector, may be configured to authenticate user credentials and may include role, task, permission, and destination parameters. Additional examples of connectors may include diary mobile applications, wearable devices, lab information systems, direct integrations with electronic health records, excel uploads, and the like.

At block 410 of the method 400 in FIG. 4, the method includes receiving a first document from a device driver associated with a hardware device. For example, an eBinder server may receive a first document from a device driver associated with a hardware device. The first document may be an image of a document generated by the device driver, and the image may include metadata. The device driver may be a printer driver associated with a remote computer and may be installed on a local user device of the sender. The hardware device may be a computer, a fax machine, or another user device.

Block 420 of the method 400 includes identifying a clinical trial identifier associated with the first document based at least in part on metadata associated with the first document. For example, a clinical trial identifier may be identified based at least in part on a connector with which a document was imported or created. In some instances, a document may automatically be assigned a clinical trial identifier, and in other instances, a document may be unassigned until a clinical trial identifier is associated with a document. For example, in instances where the hardware device is a fax machine, a clinical trial identifier may be identified based at least in part on a telephone number associated with the fax machine. Each clinical trial may be associated with a fax telephone number, or a fax telephone number may be shared across multiple clinical trials for a clinical trial site. In another example, a clinical trial identifier may be identified by first identifying a user account associated with the first document, wherein the clinical trial identifier and the folder are identified based at least in part on the user account. For example, a sender's email address may be associated with a particular clinical trial, and as a result, the clinical trial identifier may be identified based at least in part on the sender's (or receiver's) email address.

Block 430 of the method 400 includes determining a first document type of the first document by analyzing contents of the first document. Certain embodiments may determine a type of document based at least in part on content in the document, such as by parsing the document to identify one or more keywords. Other embodiments may determine a document type based at least in part on a connector through which the document was received. For example, a document received via an eFax connector or a fax machine may have a machine readable barcode or other indicia that indicates a document type, while a document type of a document received via email may be determined by either parsing contents of the email or the document. Metadata may also be used to determine a document type. For example, a document type of lab results may be identified by analyzing metadata of a document, where the metadata includes lab result indicators or related terms.

Block 440 of the method 400 includes identifying a folder associated with the clinical trial identifier at which to store the first document based at least in part on the first document type. For example, a lab result may be stored in a lab results folder for the clinical trial. In some embodiments, folders may be automatically created upon receipt of a document.

Block 450 of the method 400 includes assigning a first document state to the first document based at least in part on the first document type of the first document. Document states may indicate a status of a document. For example, a document state may include unassigned, indicating that the document is not assigned to a clinical trial, in queue, indicating that the document is associated with a clinical trial, or other document states such as signature requested, finalized, archived, destroyed, approved, or other states. A signature requested document state may indicate that a document needs to be signed by an authorized user. A document with a signature requested document state may be prevented from further processing until signed. Document states may further indicate whether a dry signature or wet signature is needed for a document, and may be determined in some embodiments by a document type and rules associated with certain document types. A finalized document may indicate that the document carries a set of access or task permissions, such as being authorized for sharing with a monitor. In some embodiments, documents that are not finalized may not be shared with other users. An archived document state may indicate that a document is no longer actively used but is available for future reference. A destroyed document state may indicate that a document no longer exists and cannot be retrieved. An approved document state may indicate that a document does not need a signature and can be finalized. Document states may be affected by and/or modified as a result of a change in task state. For example, permissions to access or read/write to a document may be modified based at least in part on a task state assigning a task to a particular user. For example, a user may not have permission to modify a document until the user is assigned a task of modifying the document. Task states may include approval, checksum compliance, timeliness indicators (e.g., on time, expired, etc.). Task states may be affected by document states, such as when a document is filed, a task may be indicated as complete. In certain instances, creation of a task may automatically modify a document state.

Documents that have been uploaded or captured via connectors may be modified or edited based at least in part on a document type and user authorizations. Certain users may be permitted to modify documents, while other users may be restricted. Document edits may be tracked and time stamped for auditing. In some embodiments, document edits applied to one page of a multiple page document may be propagated to the remaining pages of the document and may be imprinted digitally on the document.

Figure 5:
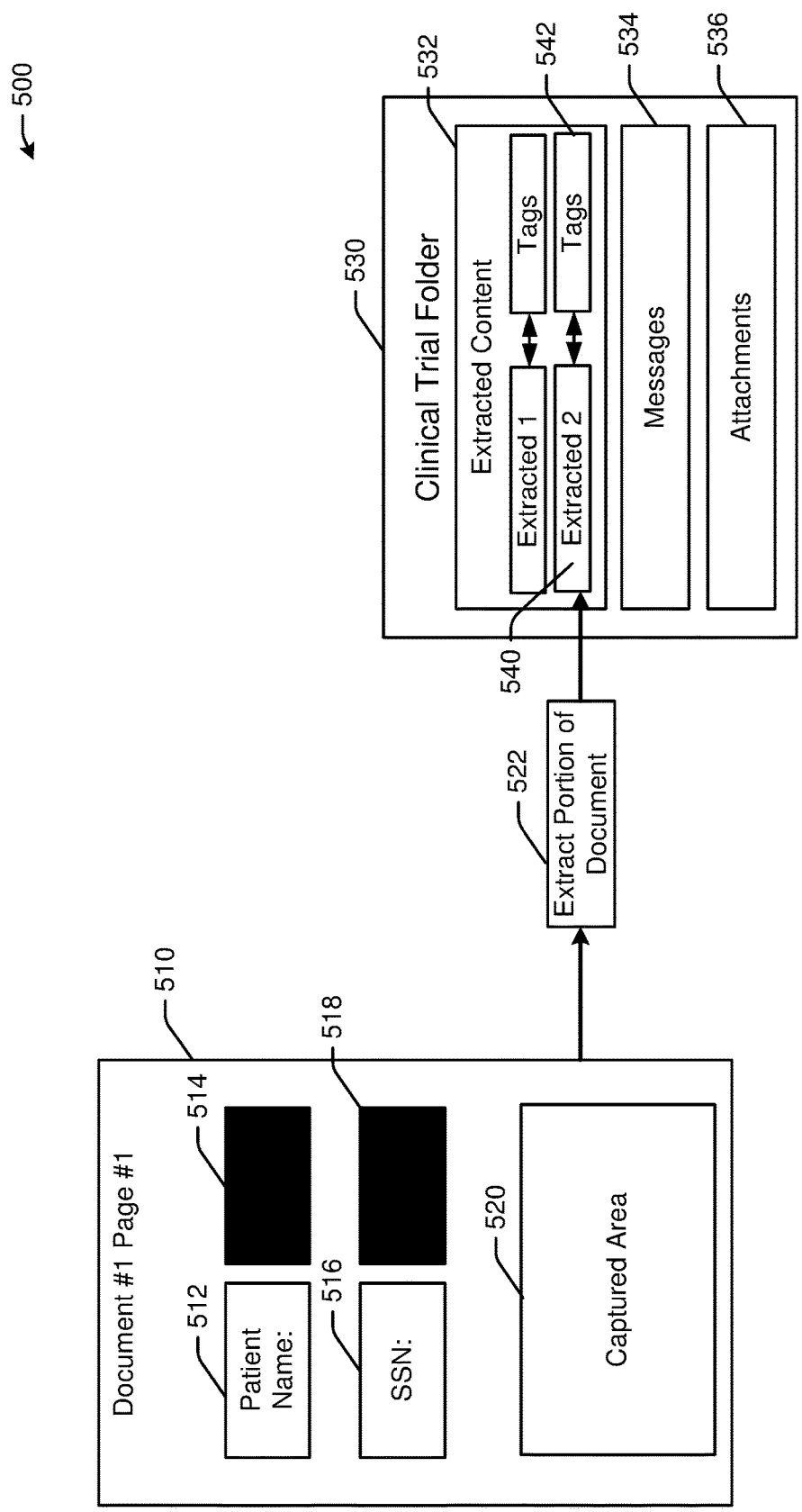
FIG. 5 is a schematic illustration of the process flow of FIG. 4 in accordance with one or more example embodiments of the disclosure.

Referring to FIG. 5, an example use case 500 of document extraction in accordance with one or more embodiments of the disclosure is depicted. Documents that are uploaded or otherwise captured by embodiments of the disclosure may be processed by extracting some or all information from the respective documents. For example, a user may desire to extract patient information from a document into another document or location. Data may be captured manually, for example by performing a gesture indicating the desired data for extraction, or automatically. For example, in FIG. 5, a document 510 may include a first label 512 indicating a patient name 514 that may be redacted, a second label 516 indicating a social security number 518 that may be redacted, and other content. A user may capture a portion 520, such as glyphs or text, of the document 510 for extraction. In one embodiment, the portion 520 may be extracted by executing computer-executable instructions of the document management module(s) 254 of a eBinder server.

The portion 520 of the document 510 may be extracted at operation 522 and may be stored in a clinical trial folder 530 that is associated with the document 510. To extract the portion 520, embodiments of the disclosure may implement various functionality. In one example, optical character recognition may be performed on a document or image, and additional metadata about the document may be analyzed, including full image text, document template information, and other metadata. The full document may be analyzed to extract the portion 520 and to generate full document text. A comparison of the full document text may be performed to validate the accuracy of the optical character recognition process. In instances where text is extracted from a specific area of an image enclosed by rectangular coordinates, optical character recognition on the enclosed area may be compared with the full text of the document. If there is a full match (e.g., 100%) of a section of the text with the extracted section with the optical character recognition tool, the data may be indicated as accurate. If there was a close match, (e.g., 90%), then additional analysis to detect common errors, such as "i" interpreted as "l", or as a pipe character. Additional analysis may be iteratively performed to generate a full match with a portion of the text that corresponds to the full text of the image.

The clinical trial folder 530 may include an extracted content section or subfolder 532, a messages section or subfolder 534, and an attachments section or subfolder 536. The extracted content section 532 may include content that has been extracted from certain documents for a clinical trial. In FIG. 5, the extracted portion 522 may be stored in the extracted content section 532 at extracted content 540 and may be associated with tags 542. Tags, such as tags 542, may be configured to organize, group, and/or share documents or portions of documents based on tags. Tags may facilitate searching for particular types or groups of documents. Tags may further provide read access permissions and access window information indicating a length of time that a document is accessible to a user with permission. Documents may further be exported by tags (e.g., into a zip file with pdf documents, etc.). The messages section 534 of the clinical trial folder 530 may include captured messages between parties to the clinical trial, and the attachments section 536 may include attachments that were captured from messages 534.

In some embodiments, documents may contain multiple pages. A user may identify a portion of a first page of the document to extract, and embodiments of the disclosure may automatically spatially propagate the captured area, such as the captured area 520 in FIG. 5, across each of the pages in the document. Coordinates of a captured area may be reproduced across each page in a document. An example method of document extraction may be implemented by executing computer-executable instructions of the document management module(s) 254, for example, where the method includes extracting a portion of a first document based at least in part on a document type to generate extracted content, associating one or more tags with the extracted content, where the one or more tags include at least one access permission rule and a document category indication, and storing the extracted content and one or more tags in the folder.

Figure 6:
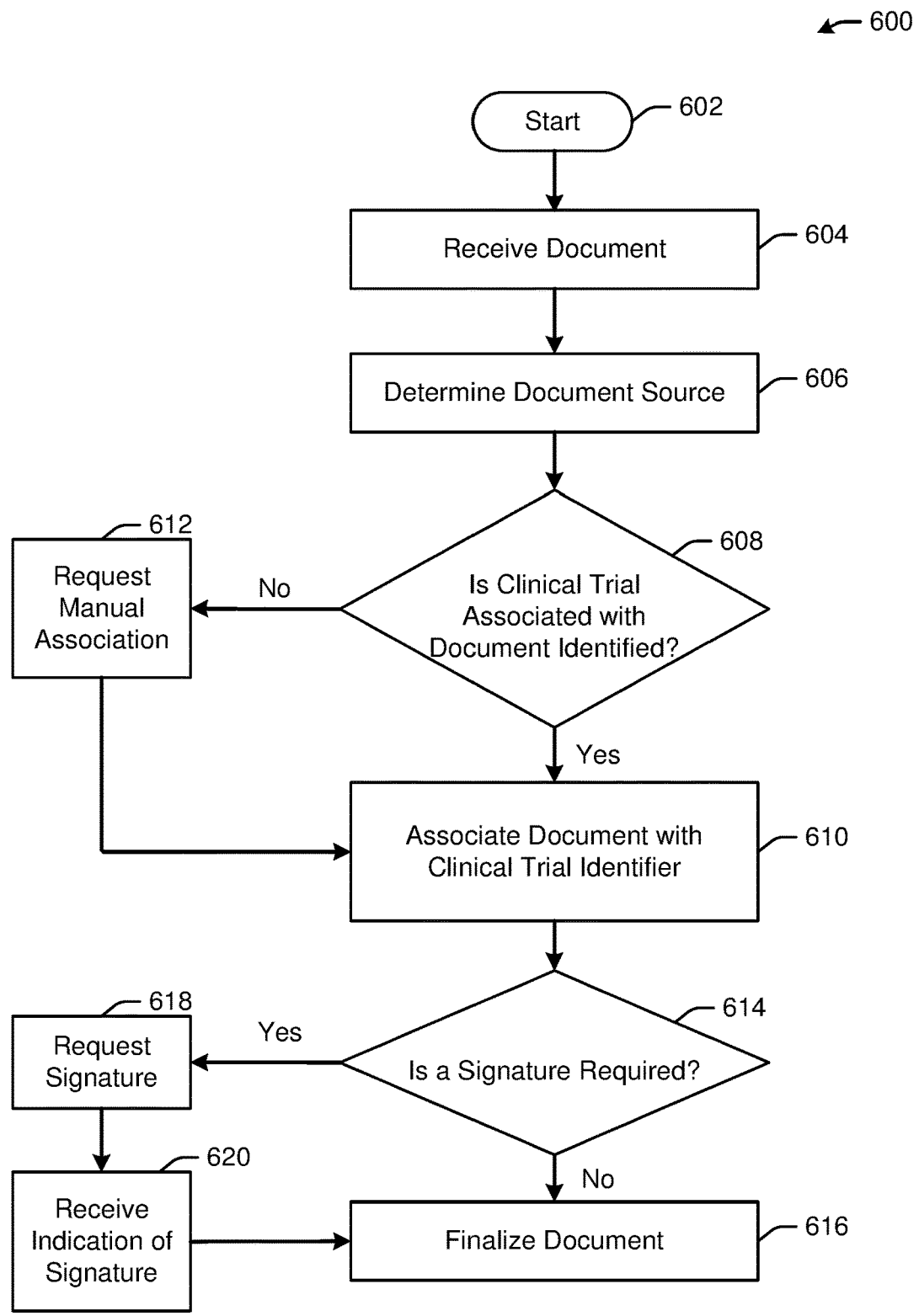
FIG. 6 is an example process flow diagram of an illustrative method for remote monitoring and dynamic document management in accordance with one or more example embodiments of the disclosure.

FIG. 6 illustrates an example process flow 600 for document management in accordance with one or more embodiments. The process flow 600 may start at block 602. At block 604 a document may be received, for example by a eBinder server as described herein. At block 606, a document source may be determined. For example, a document source may be a doctor office, an imaging system, a lab result, and the like. At determination block 608, a determination is made, for example by the document management module(s) 252 of a eBinder server, of whether a clinical trial associated with the received document has been identified. If the clinical trial has been identified, for example via analysis of the document or based at least in part on a connector through which the document was received, the process flow 600 proceeds to block 610, where the document is associated with the clinical trial identifier. If the clinical trial has not been identified, the process flow 600 proceeds to block 612, at which manual association of the document with a clinical trial is requested. In some embodiment, the document may be in an unassigned document state until the document is manually associated. Upon determining that the document has been manually associated with a clinical trial, the process flow 600 proceeds to determination block 614, at which a determination is made as to whether a signature is required for the document. For example, the determination may be made by the document management module(s) 252 and may be based at least in part on a document type of the document, as well as document signature rule(s) 266. If no signature is required the process flow 600 may proceed to block 616, at which the document may be finalized and assigned a finalized state. If a signature is required, the process flow 600 may proceed to block 618 at which a signature may be requested from a party. The party may be identified based at least in part on the document type and/or rules and a notification requesting a signature may be sent to the appropriate party. In one example, computer-executable instructions of the document management module(s) 254 may be executed to determine that execution of a document is required based at least in part on the document type and/or one or more rules, such as the document signature rule(s) 266, associated with the document type. Embodiments may determine that the document is unexecuted based at least in part on the document state, and may send a request for execution to a user account associated with the clinical trial identifier for a user from which a signature is required. At block 620 an indication of a signature may be received and the process flow 600 may proceed to block 616 at which the document is finalized. For example, an execution notification indicating that the document has been executed may be received, and a second document state, such as a finalized state, may be assigned to the document. In some embodiments, upon determining that a document is in a finalized state, a finalized notification may be sent to a user account indicating the document is available for review. Documents that are available for review may be available or otherwise accessible for a predetermined length of time in some embodiments. For example, a document may be shared with a particular user or group of users for a time period of 1 week, while other users may access the document for 1 year. Documents that are finalized may be automatically archived and/or destroyed after a predetermined amount of time. In one example, documents may be automatically destroyed after a regulatory time period of 7 years.

Access to documents may be controlled by user permissions associated with user accounts. In order to access documents, in one example, embodiments of the disclosure may receive an access request to access a document, identify a user account associated with the access request, and determine that the user account is authorized to access the document or perform other tasks within the system.

Figure 7:
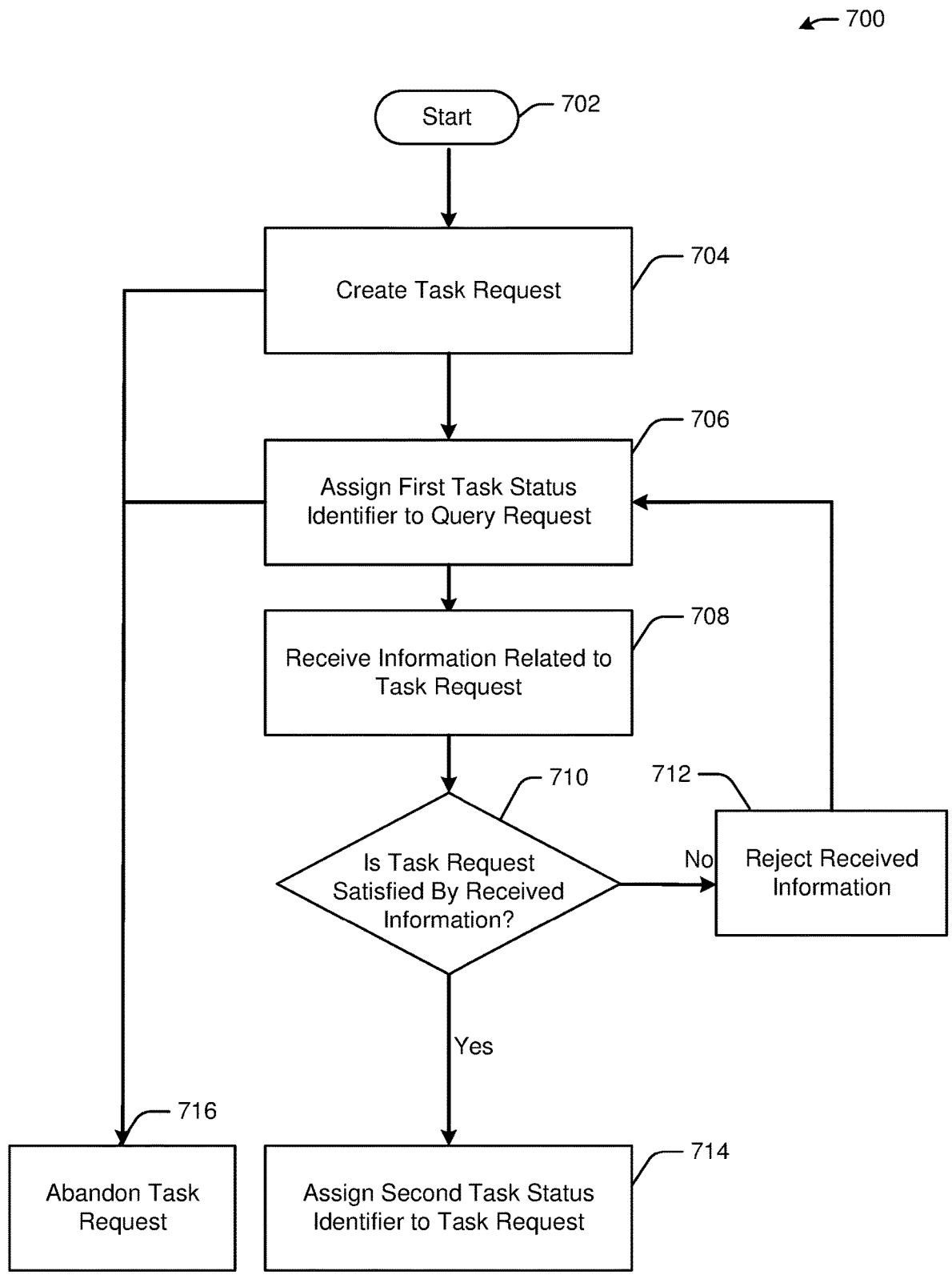
FIG. 7 is an example process flow diagram of an illustrative method for remote monitoring and dynamic document management in accordance with one or more example embodiments of the disclosure.

FIG. 7 depicts a schematic illustration of a process flow 700 for managing queries associated with a clinical trial. In FIG. 7, computer-executable instructions of one or more module(s) of a eBinder server, such as the task management module(s) 252 of the eBinder server 200 of FIGS. 2-3, may be executed to manage task requests for information that a monitor may submit to a clinical trial site or coordinator. By fulfilling queries, a clinical trial site may facilitate identification of potential risks on the clinical trial. Tracking of queries further facilitates identification of risks of a clinical trial by sponsors, coordinators, and investigators, and allows implementation of corrective action. Task response timeliness and/or completeness may facilitate evaluation of a clinical trial site performance quality. Coordinators may desire to fulfill task requests by providing documents as evidence for a monitor in order to complete source document verification.

The process flow 700 may start at block 702. At block 704, a task request may be created. Research sites or clinical trial sites may authorize monitors to generate a task request, which may be placed in a queue that includes all task requests for a clinical trial. Each task request may have a specific lifecycle. Upon creating the task request, the process flow 700 may proceed to block 706, at which the task request is assigned a first task status identifier. Alternately, if a monitor decides that the task is no longer needed, the process flow 700 may proceed to block 716, at which the task request is abandoned. Task statuses and related status identifiers may include in progress, indicating that the task is in the process of being addressed, complete, indicating that the task has been completed by a coordinator and a monitor may validate the documents provided by the coordinator, rejected, indicating that a monitor has rejected a task response as incomplete or incorrect, abandoned, closed, or other task statuses.

Upon assigning a first task status identifier to the task request, the process flow 700 may proceed to block 708, at which information related to the task request is received. Information may include documents, evidence, data, and the like. For example, a coordinator may provide information in response to a task request. At determination block 710, a determination may be made whether the task request is satisfied by the received information. In one example, the determination may be made automatically by the task management module(s) 252. In another example, a monitor may review the information provided by the coordinator and may determine if the task request is satisfied. If the task request is not satisfied, the process flow 700 may proceed to block 712, at which the received information is rejected, and the process flow may return to block 706. If the task request is satisfied, the process flow 700 may proceed to block 714, at which a second task status identifier, such as complete, is assigned to the task request. The second task identifier may be different than the first task identifier. Access to documents provided in response to queries may be controlled by user permissions associated with user accounts, as described herein.

Figure 8:
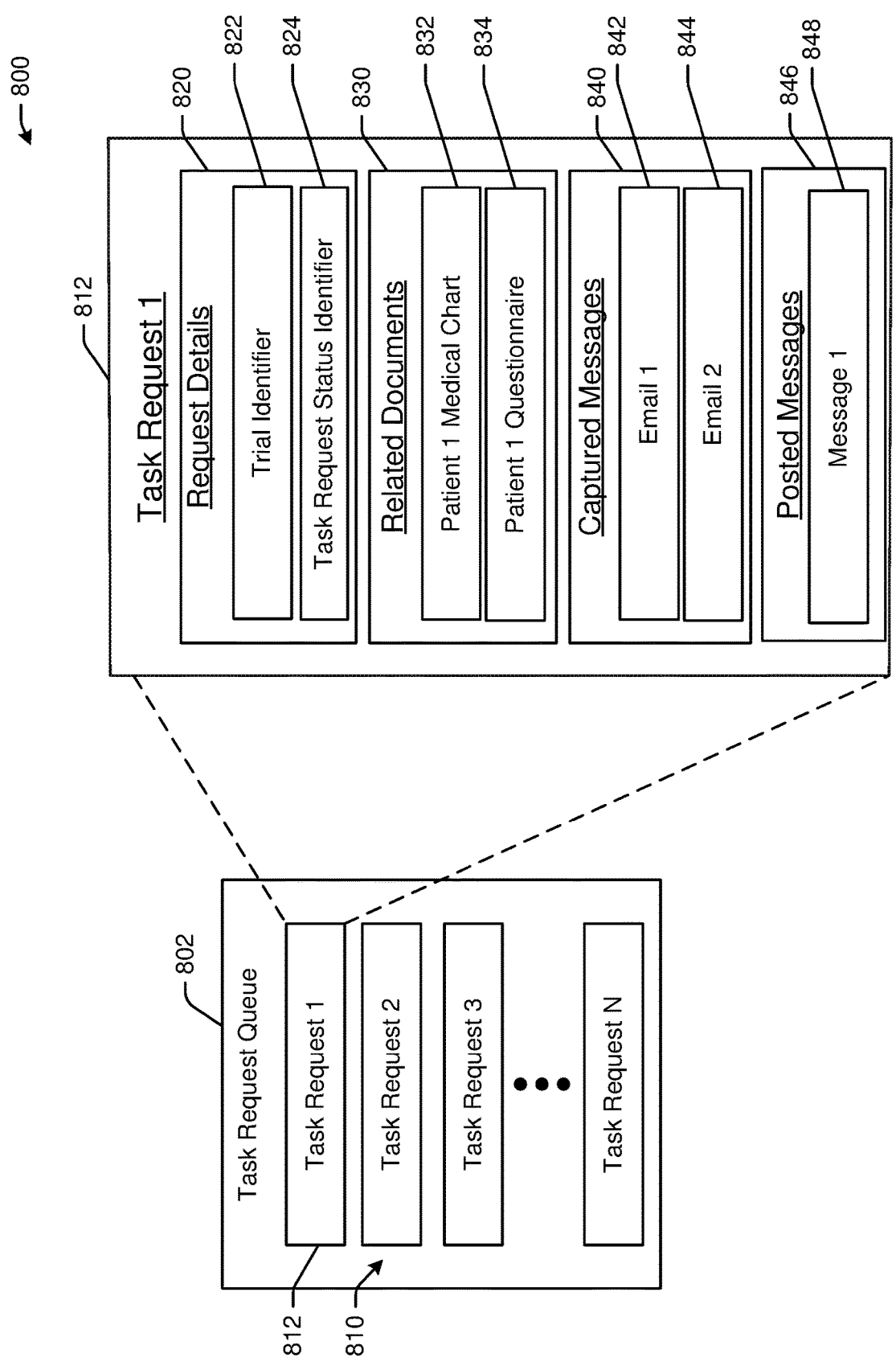
FIG. 8 is a schematic illustration of the process flow of FIG. 7 in accordance with one or more example embodiments of the disclosure.

FIG. 8 illustrates an example use case of task management 800 in accordance with one or more embodiments of the disclosure. In FIG. 8, a eBinder server may receive a task request 812 from a first user account, such as a monitor user account, where the task request includes request details 820 such as a patient identifier and/or a clinical trial identifier 822. In one example, text may be parsed to identify a patient or clinical trial identifier, date range, or other information in a task request or response. Some embodiments may utilize stack overflow to extract keywords to provide information to a requester including potential answers to a task request before the request is submitted to avoid duplicate requests or to facilitate timely responses to queries. The eBinder server may determine a document type associated with the task request, which may be a type of document that the task request is requesting. For example, the task request may request a lab result document type. The eBinder server may determine that the task request is associated with the particular clinical trial identifier 822 and may add the task request to a task request queue 802 associated with the clinical trial identifier and/or the patient identifier. The task request queue 802 may include multiple task requests 810. The eBinder server may assign a first task status identifier 824, such as in progress, to the task request 812 indicating the task request 812 is unaddressed. The eBinder server may receive a document in response to the task request, for example from a coordinator, and may prevent the first user account, or monitor user account, from accessing the document, based at least in part on the first task status identifier. For example, the coordinator may desire to provide additional documents and may not indicate the response is complete, in which instance the monitor may not access the document. In other embodiments, the monitor may be able to view documents as they are uploaded by the coordinator. In some embodiments, the eBinder server may determine that a document uploaded by a coordinator in response to a task request matches a document type associated with the task request, and may associate the uploaded document with the task request. The eBinder server may assign a second task status identifier to the task request indicating that the task request is addressed based at least in part on the uploaded document and document type, and may facilitate access to the uploaded document by the monitor based at least in part on the second task status identifier.

In FIG. 8, the task request 812 may include related documents 830 that may be uploaded by a coordinator or monitor and may include, for example, a medical chart 832, a patient questionnaire 834, captured messages 840 between the coordinator and monitor related to the task request 812, and posted messages 846 which may be posted directly to the system by either party. The captured messages 840 may include emails 842, 844 that may be identified and/or captured as described herein. The posted messages 846 may include message 848 that may be posted rather than emailed between parties.

Figure 9:
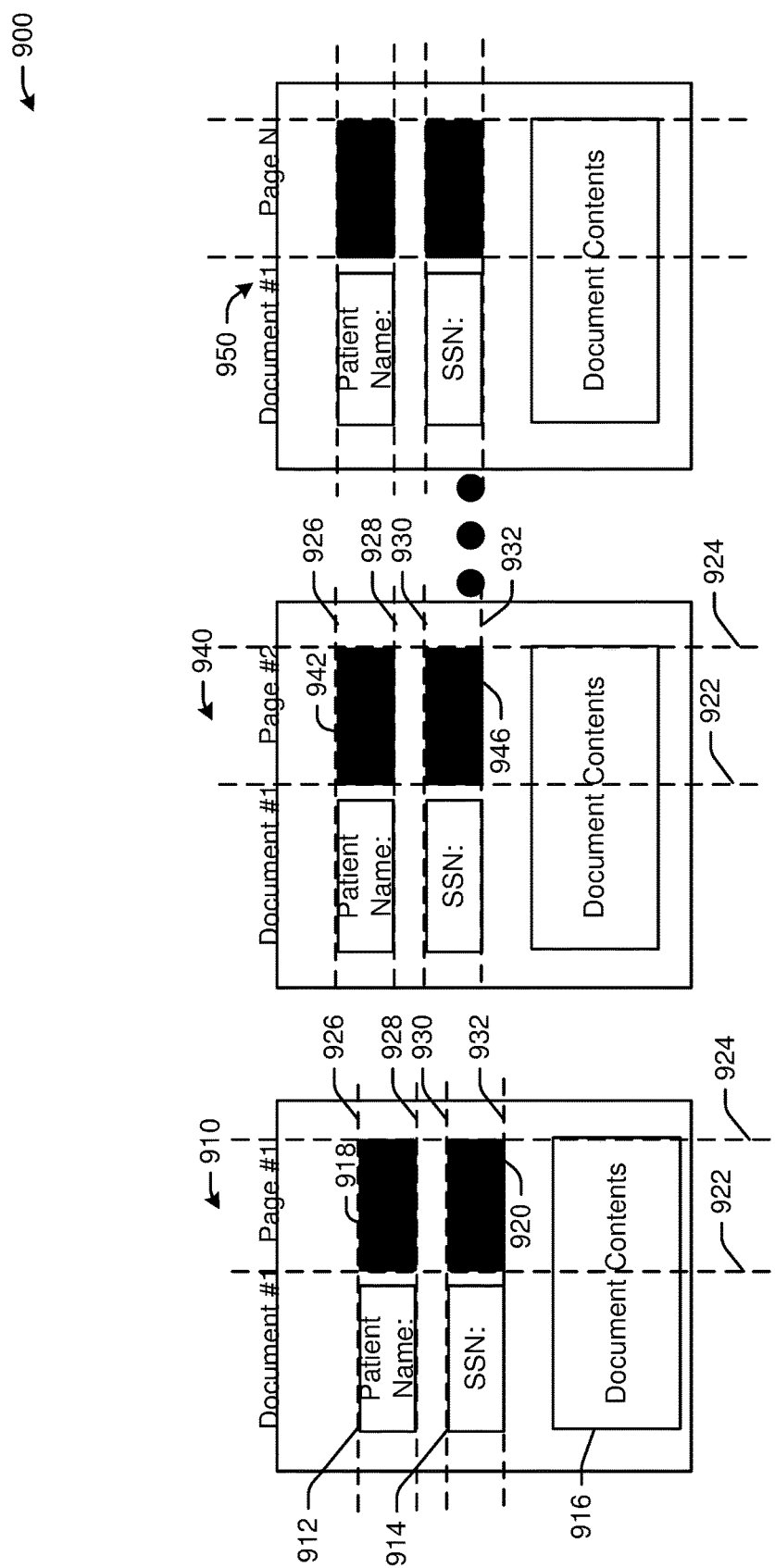
FIG. 9 is a schematic illustration of an example use case for redaction and spatial propagation of documents in accordance with one or more example embodiments of the disclosure.

FIG. 9 depicts a schematic illustration of a method of document redaction in accordance with one or more embodiments of the disclosure. Redaction may protect sensitive information, such as a patient name or contact information. Embodiments of the disclosure may facilitate manual redaction and automatic redaction of portions of documents. In FIG. 9, an example use case 900 includes a document first page 910 with a patient name 912, a social security number 914, and document contents 916. A user may redact a portion of the page 910 by identifying coordinates on the page 910 which are to be redacted. For example, a user may indicate a first vertical grid line 922 and a second vertical grid line 924, and a first horizontal line 926 and a second horizontal line 928 to identify a first redaction area 918 on the page 910. In one example, a user may click and drag to identify the first redaction area 918 for redaction. The user may identify a second redaction area 920 using the first vertical grid line 922, the second vertical grid line 924, a third horizontal line 930, and a fourth horizontal line 932. The first redaction area 918 may correspond to the patient name 912 and the second redaction area 920 may correspond to the social security number.

The first redaction area 918 and the second redaction area 920 may be spatially propagated to the remaining pages in the document. For example, at a second page 940, the grid lines identified by the user to identify the redaction areas may be applied to identify a third redaction area 942 on the second page 940 that corresponds to the first redaction area 918 on the first page 910, and a fourth redaction area 946 that corresponds to the second redaction area 920. Similarly, the redaction areas may be applied to a third page 950 in the document. An example method of spatial propagation for redaction includes receiving a redaction request with a selection of a portion of a first page for redaction, determining that the user account is authorized to redact the document, redacting the selected portion of the first page of the document by determining a set of coordinates associated with the selected portion, identifying the set of coordinates on the second page of the first document, and automatically redacting the second page of the first document based at least in part on the identified set of coordinates. Accordingly, patient names on each page of the document may be redacted without manual redaction of each page by the user.

Redaction may also be completed by searching for keywords by obtaining coordinates on each document page for a keyword. In some embodiments, users may have an option to confirm redaction after searching for keywords. Some embodiments may further generate redaction templates that may be implemented by users. For example, electronic health records from a particular source may be associated with a redaction template that can be automatically applied by a user without manual identification of redaction areas on document pages. For example, some embodiments may automatically redact a portion of a document based at least in part on the document type or a document source. Keyword redaction may be facilitated by optical character recognition as described above. In instances where words are detected on an image for automatic redaction, iterative analysis and processing may be performed to generate a match in the text of the whole document. Alternatively, by knowing the template of a document, the type of information expected in different coordinates of the image (e.g., numeric values for fields in the lab values) may be leveraged to assist with correcting optical character recognition extractions.

Embodiments of the disclosure may perform post redaction processing. For example, after a portion of a document has been redacted, an image of the document with the redacted portion may be generated, so as to prevent unauthorized users from accessing the redacted information. Generating an image of the redacted document may result in deletion of the underlying data that has been redacted. In other embodiments, a new version of a document may be created with new and independent permission and access controls instead of generating an image.

Metadata may be generated for a redacted document after redaction is complete. To ensure that metadata does not include redacted information, embodiments of the disclosure may perform optical character recognition on both the original document and the redacted document. Outputs of the optical character recognition may be compared, and the text included on the original document that is not found in the redacted document may be flagged as confidential. Text may include any sequence of characters, as well as inline images, such as emojis. Metadata for the redacted document may be scrubbed to remove any flagged text, thereby ensuring that the redacted document does not include any accessible redacted information. All metadata may be indexed and searchable, so as to increase system functionality.

In other embodiments, security of redacted information may be maintained by identifying character locations for one or more characters that are redacted. For example, positioning information, such as bitmap information, for a bounding box generated about redacted information may be determined for a redacted document. Based at least in part on the bounding box positioning, characters or text originally positioned within the bounding box may be flagged as redacted information, and may therefore be scrubbed from metadata associated with the redacted document.

Figure 10:
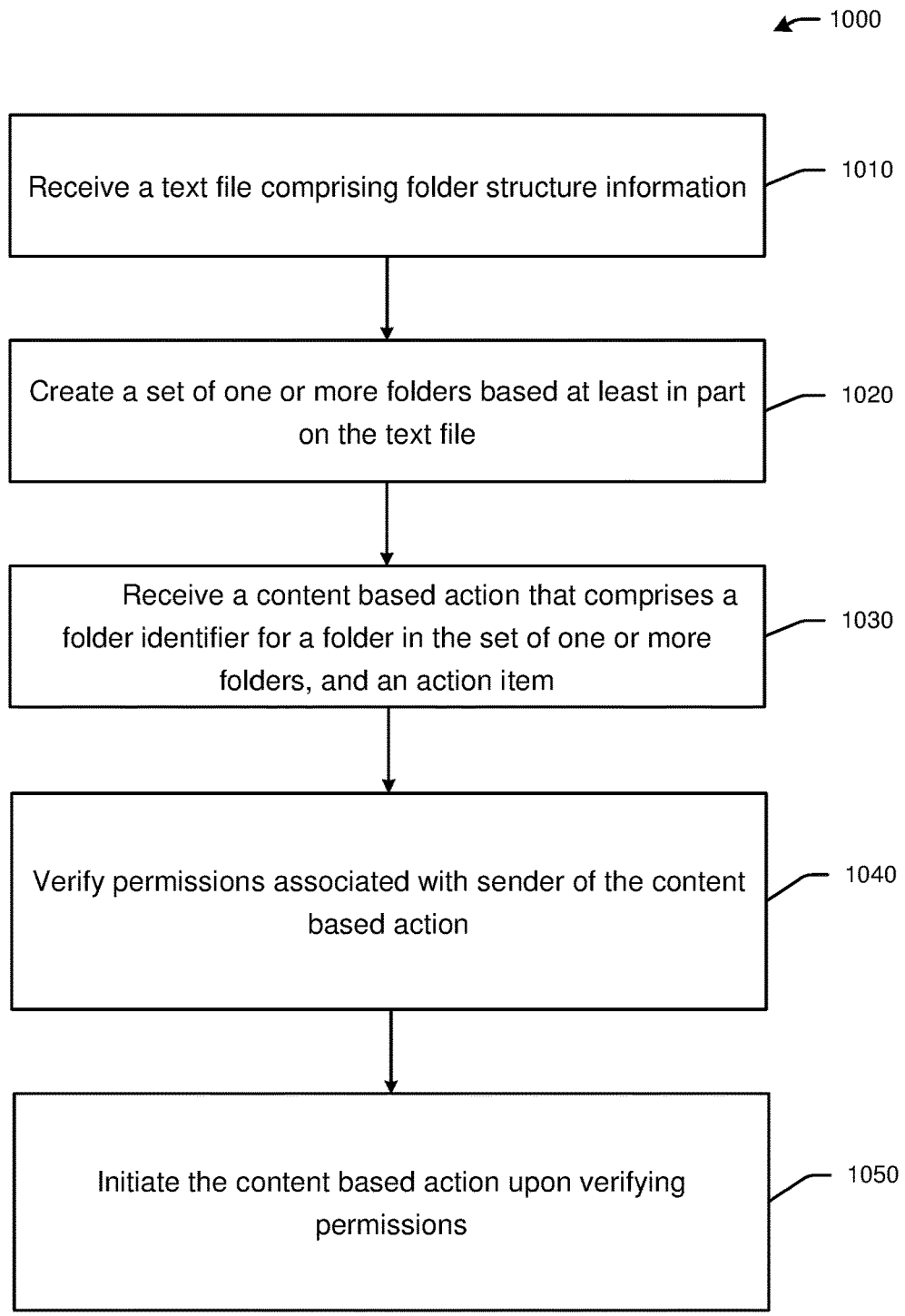
FIG. 10 is an example process flow diagram of automatic cloud-based document categorization and management in accordance with one or more example embodiments of the disclosure.

FIG. 10 is an example process flow diagram of automatic cloud-based document categorization and management in accordance with one or more example embodiments of the disclosure. At block 1010, a text file comprising a folder structure is received. The text file may include one or more lines of text representing nested folders as indicated by a number of spaces or tabs preceding a filename. Other embodiments may use different characters to represent folder structure in the text file.

At block 1020, a set of folders is created on a cloud-based system based at least in part on the text file.

At block 1030, a content based action is received comprising a folder identifier and an action item. For example, content based actions may be received via email, fax, eFax, or another communication medium. Content based actions may include actions such as "replace," "archive," "move," or instructions such as "do not delete." Content based actions may be provided within contents of a document, such as in a header, or within the communication, such as in an email subject or body. Content based actions may indicate an action the cloud-based server is to initiate upon receipt of the instructions. For example, the content based action may request that the cloud-based server replace a file previously stored at the cloud-based server with another file that is attached to the communication. In another example, the content based action may request that the cloud-based server store an attached file in a particular folder on the cloud-based server. Other examples may include setting or modifying expiration dates of files, modifying permissions to access, or other action items.

At block 1040, permissions associated with an instructor or a sender from which the content based action was received may be verified. Permissions verification may be used to ensure authorized access to privileged information.

At block 1050, the requested action may be initiated. For example, the cloud-based server may receive a request to replace a file stored on the cloud-based server with a new file. Upon verification of the sender's permissions, the cloud-based server may replace the pre-existing file with the new file provided by the user. Embodiments of the disclosure may allow one or more action items to be triggered via document content, email, or another communication medium.

One or more operations of the process flows or use cases of FIGS. 2-10 may have been described above as being performed by a user device, or more specifically, by one or more program modules, applications, or the like executing on a device. It should be appreciated, however, that any of the operations of process flows or use cases of FIGS. 2-10 may be performed, at least in part, in a distributed manner by one or more other devices, or more specifically, by one or more program modules, applications, or the like executing on such devices. In addition, it should be appreciated that processing performed in response to execution of computer-executable instructions provided as part of an application, program module, or the like may be interchangeably described herein as being performed by the application or the program module itself or by a device on which the application, program module, or the like is executing. While the operations of the process flows or use cases of FIGS. 2-10 may be described in the context of the illustrative eBinder server, it should be appreciated that such operations may be implemented in connection with numerous other device configurations.

The operations described and depicted in the illustrative process flows or use cases of FIGS. 2-10 may be carried out or performed in any suitable order as desired in various example embodiments of the disclosure. Additionally, in certain example embodiments, at least a portion of the operations may be carried out in parallel. Furthermore, in certain example embodiments, less, more, or different operations than those depicted in FIGS. 2-10 may be performed.

Although specific embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure.

Certain aspects of the disclosure are described above with reference to block and flow diagrams of systems, methods, apparatuses, and/or computer program products according to example embodiments. It will be understood that one or more blocks of the block diagrams and flow diagrams, and combinations of blocks in the block diagrams and the flow diagrams, respectively, may be implemented by execution of computer-executable program instructions. Likewise, some blocks of the block diagrams and flow diagrams may not necessarily need to be performed in the order presented, or may not necessarily need to be performed at all, according to some embodiments. Further, additional components and/or operations beyond those depicted in blocks of the block and/or flow diagrams may be present in certain embodiments.

Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, may be implemented by special-purpose, hardware-based computer systems that perform the specified functions, elements or steps, or combinations of special-purpose hardware and computer instructions.

That which is claimed is:

1. A method comprising:

receiving, by a computer system comprising one or more computer processors coupled to at least one memory, a first document;

determining, by the computer system, user permissions to access the first document;

identifying, by the computer system, a clinical trial identifier associated with the first document based at least in part on metadata associated with the first document;

determining, by the computer system, that a document type of the first document is a first document type by analyzing contents of the first document;

identifying, by the computer system, a folder associated with the clinical trial identifier at which to store the first document based at least in part on the first document type;

assigning, by the computer system, a first document state to the first document based at least in part on the first document type of the first document;

determining, by the computer system, a set of coordinates corresponding to a portion of the first document to be redacted based at least in part on the document type or a document source of the first document, wherein determining the set of coordinates comprises determining a user input on a user interface of a first vertical grid line, a second vertical grid line, a first horizontal grid line, and a second horizontal grid line, wherein the grid lines together identify a redaction area corresponding to the portion of the first document; and automatically redacting, by the computer system, the portion of the first document and a corresponding portion of a second document using the set of coordinates.

2. The method of claim 1, further comprising:

determining, by the computer system, that execution of the first document is required based at least in part on the first document type and one or more rules associated with the first document type;

determining, by the computer system, that the first document is unexecuted based at least in part on the first document state; and sending, by the computer system, a request for execution to a first user account associated with the clinical trial identifier.

3. The method of claim 2, further comprising:

receiving, by the computer system, an execution notification indicating that the first document has been executed;

assigning, by the computer system, a second document state to the first document.

4. The method of claim 3, further comprising:

sending, by the computer system, a finalized notification to a second user account indicating the first document is available for review.

5. The method of claim 1, further comprising:

receiving, by the computer system, an access request to access the first document;

identifying, by the computer system, a user account associated with the access request; and determining, by the computer system, that the user account is authorized to access the first document.

6. The method of claim 5, wherein the first document comprises a first page and a second page, and the method further comprises:

receiving, by the computer system, a redaction request comprising a selection of a portion of the first page for redaction;

determining, by the computer system, that the user account is authorized to redact the first document;

redacting, by the computer system, the selected portion of the first page of the document by determining a set of coordinates associated with the selected portion;

identifying, by the computer system, the set of coordinates on the second page of the first document; and automatically redacting, by the computer system, the second page of the first document based at least in part on the identified set of coordinates.

7. The method of claim 1, further comprising:

extracting, by the computer system, a portion of the first document based at least in part on the document type to generate extracted content;

associating, by the computer system, one or more tags with the extracted content, wherein the one or more tags comprise at least one access permission rule and a document category indication; and storing, by the computer system, the extracted content and one or more tags in the folder.

8. The method of claim 1, further comprising:

receiving, by the computer system, a task request from a first user account, wherein the task request comprises a patient identifier;

determining, by the computer system, a second document type associated with the task request;

determining, by the computer system, that the task request is associated with the clinical trial identifier;

adding, by the computer system, the task request to a task queue associated with the clinical trial identifier and the patient identifier;

assigning, by the computer system, a first task status identifier to the task request indicating the task request is unaddressed;

receiving, by the computer system, a second document in response to the task request; and preventing, by the computer system, the first user account from accessing the second document, based at least in part on the first task status identifier.

9. The method of claim 8, further comprising:

determining, by the computer system, that the second document matches the second document type;

associating, by the computer system, the second document with the task request;

assigning, a second task status identifier to the task request indicating that the task request is addressed;

facilitating, by the computer system, access to the second document by the first user account based at least in part on the second task status identifier; and generating, by the computer system, a responsiveness metric associated with the clinical trial identifier based at least in part on an elapsed time between the task request and receiving of the second document.

10. The method of claim 1, further comprising:

identifying, by the computer system, a user account associated with the first document, wherein the clinical trial identifier and the folder are identified based at least in part on the user account.

11. The method of claim 1, wherein the first document is received from a device driver associated with a hardware device.

12. The method of claim 11, wherein either:

(i) the device driver is a printer driver associated with a remote computer; or (ii) the hardware device is a fax machine, and the clinical trial identifier is identified based at least in part on a telephone number associated with the fax machine.

13. The method of claim 11, wherein the first document is an image of a document generated by the device driver and the image comprises metadata.

14. The method of claim 1, further comprising:

determining, by the computer system, first text included in the first document;

redacting, by the computer system, a portion of the first document to generate a second document;

determining second text included in the second document;

determining a set of redacted text based at least in part on a comparison of the first text and the second text; and removing the set of redacted text from metadata associated with the second document.

15. A method comprising:

receiving, by a computer system comprising one or more computer processors coupled to at least one memory, a first email from a first user account, the first email comprising text and an attached file, wherein the attached file comprises a first page and a second page;

managing, by the computer system, user permission to access the first email;

identifying, by the computer system, a clinical trial identifier associated with the first email based at least in part on the first user account, the text, or the attached file;

determining, by the computer system, a set of coordinates corresponding to a portion of the first page to be redacted based at least in part on a document type or a document source of the attached file, wherein determining the set of coordinates comprises determining a user input on a user interface of a first vertical grid line, a second vertical grid line, a first horizontal grid line, and a second horizontal grid line, wherein the grid lines together identify a redaction area corresponding to the portion of the first page;

automatically redacting the portion of the attached file and a corresponding portion of the second page of the attached file using the set of coordinates based at least in part on a document type or a document source of the attached file;

storing, by the computer system, a copy of the first email and a redacted version of the attached file in a folder associated with the clinical trial identifier;

identifying, by the computer system, a second user account indicative of an intended recipient of the first email;

identifying, by the computer system, an email address associated with the second user account; and forwarding, by the computer system, the first email to the email address.

16. The method of claim 15, further comprising:

receiving, by the computer system, a second email from the email address of the second user account;

determining, by the computer system, that the second email is a reply to the first email;

storing, by the computer system, the second email in the folder; and forwarding, by the computer system, the second email to the first user account.

17. A system comprising:

at least one memory storing computer-executable instructions; and at least one processor communicatively coupled to the at least one memory and configured to access the at least one memory and execute the computer-executable instructions to:

receive a first document from a device driver associated with a hardware device;

manage user permission to access the first document;

identify a clinical trial identifier associated with the first document based at least in part on metadata associated with the first document;

determine that a document type of the first document is a first document type by analyzing contents of the first document;

identify a folder associated with the clinical trial identifier at which to store the first document based at least in part on the first document type;

assign a first document state to the first document based at least in part on the first document type of the first document;

determine a set of coordinates corresponding to a portion of the first document to be redacted based at least in part on the document type or a document source of the first document, wherein determining the set of coordinates comprises determining a user input on a user interface of a first vertical grid line, a second vertical grid line, a first horizontal grid line, and a second horizontal grid line, wherein the grid lines together identify a redaction area corresponding to the portion of the first document; and automatically redact the portion of the first document and a corresponding portion of a second document using the set of coordinates.

18. The system of claim 17, wherein the at least one processor is further configured to execute the computer-executable instructions to:

determine that execution of the first document is required based at least in part on the first document type and one or more rules associated with the first document type;

determine that the first document is unexecuted based at least in part on the first document state;

send a request for execution to a first user account associated with the clinical trial identifier;

receive an execution notification indicating that the first document has been executed; and assign a second document state to the first document.

19. The system of claim 17, wherein the at least one processor is further configured to execute the computer-executable instructions to:

identify a folder associated with the first document on a cloud-based server;

determine that a previous version of the first document is stored in the folder; and replace the previous version with the first document.

20. The system of claim 17, wherein the first document is an image of a document generated by the device driver and the image comprises metadata.

* * * * *